United States Patent
Giaquinto

(10) Patent No.: US 10,869,782 B2
(45) Date of Patent: Dec. 22, 2020

(54) EAR CLEANING DEVICE WITH WHISK-LIKE BULBOUS ENDS

(71) Applicant: Wares World Wide LLC, Trenton, NJ (US)

(72) Inventor: Giuseppina Giaquinto, Trenton, NJ (US)

(73) Assignee: Wares World Wide LLC, Trenton, NJ (US)

( * ) Notice: Subject to any disclaimer, the term of this patent is extended or adjusted under 35 U.S.C. 154(b) by 108 days.

(21) Appl. No.: 15/763,271

(22) PCT Filed: Oct. 21, 2016

(86) PCT No.: PCT/US2016/058099
§ 371 (c)(1),
(2) Date: Mar. 26, 2018

(87) PCT Pub. No.: WO2017/087123
PCT Pub. Date: May 26, 2017

(65) Prior Publication Data
US 2018/0263821 A1    Sep. 20, 2018

Related U.S. Application Data

(60) Provisional application No. 62/257,012, filed on Nov. 18, 2015.

(51) Int. Cl.
*A61F 11/00* (2006.01)
*A61F 13/38* (2006.01)

(52) U.S. Cl.
CPC ............ *A61F 11/006* (2013.01); *A61F 13/38* (2013.01)

(58) Field of Classification Search
CPC .............................. A61F 11/006; A61F 13/38
See application file for complete search history.

(56) References Cited

U.S. PATENT DOCUMENTS

| | | | |
|---|---|---|---|
| 374,026 A | 11/1887 | Williams | |
| 1,520,908 A | 12/1924 | Meyer | |
| 2,096,162 A | 10/1937 | Daley | |
| 3,923,061 A | 12/1975 | Rossignol | |
| 5,127,899 A * | 7/1992 | Schmerse, Jr. | A61F 13/38 604/1 |
| 5,452,717 A | 9/1995 | Branigan et al. | |

(Continued)

FOREIGN PATENT DOCUMENTS

| | | |
|---|---|---|
| DE | 10044582 A1 | 4/2002 |
| FR | 377752 | 7/1907 |
| FR | 58319 E | 6/1948 |

OTHER PUBLICATIONS

International Search Report and Written Opinion issued in International Application No. PCT/US16/58099 dated Jan. 17, 2017.

*Primary Examiner* — Gregory A Anderson
(74) *Attorney, Agent, or Firm* — Hoffmann & Baron, LLP

(57) ABSTRACT

The present disclosure provides for an ear cleaning device comprising an integral body, a central handle portion of the integral body that supports a first whisk-like bulbous end. The first whisk-like bulbous end is integral with the central handle portion and comprises flexible intertwined wire-like loops used in the removal of ear wax debris. The first whisk-like bulbous end is of a size that averts insertion thereof to an ear canel.

24 Claims, 4 Drawing Sheets

(56) References Cited

U.S. PATENT DOCUMENTS

| | | |
|---|---|---|
| 5,632,756 A | 5/1997 | Kruglick |
| 5,715,559 A | 2/1998 | Mitri |
| 5,715,850 A * | 2/1998 | Markgraaf ............ A61F 11/006 132/333 |
| 7,658,745 B2 | 2/2010 | Olson |
| 7,951,106 B1 | 5/2011 | Perez et al. |
| 2003/0135228 A1 | 7/2003 | Crespo |
| 2005/0096678 A1 | 5/2005 | Olson |
| 2008/0142385 A1 | 6/2008 | Stein et al. |
| 2009/0112241 A1 | 4/2009 | Bar et al. |
| 2014/0031846 A1 | 1/2014 | Edme et al. |
| 2014/0200600 A1 | 7/2014 | Blatstein |

* cited by examiner

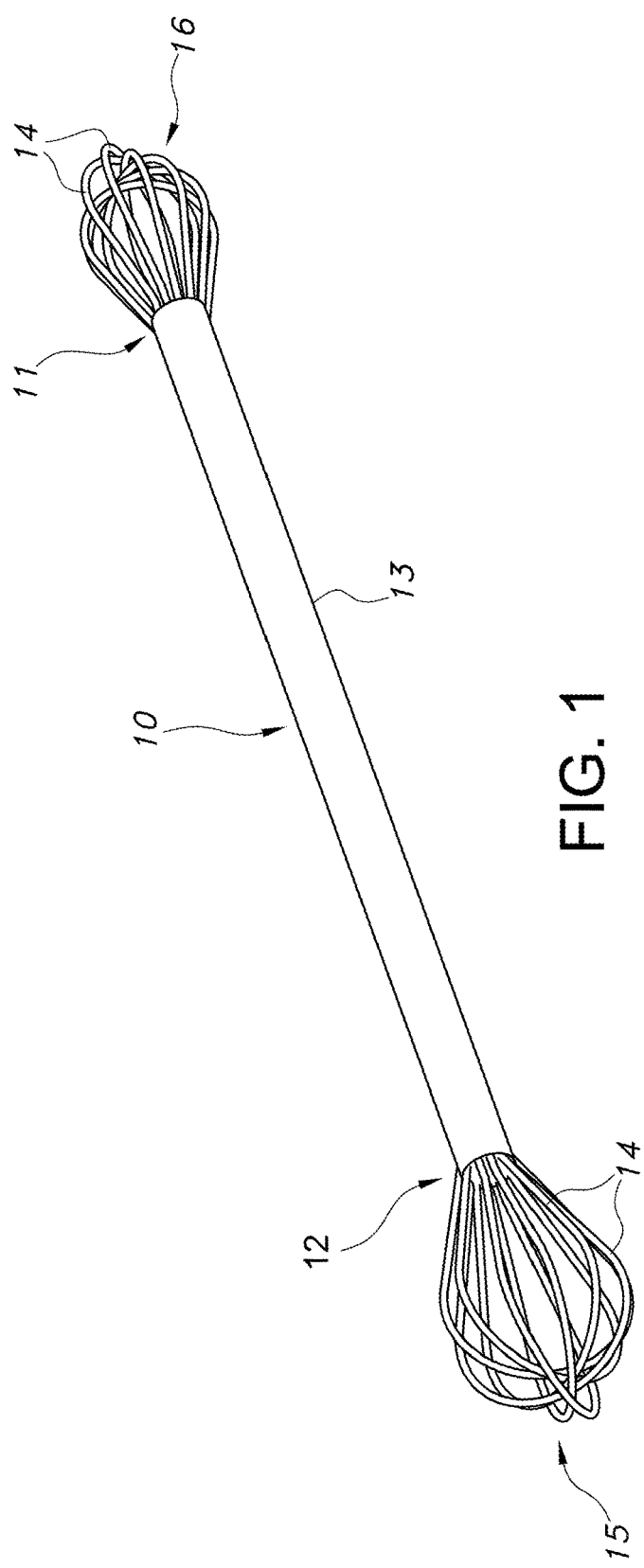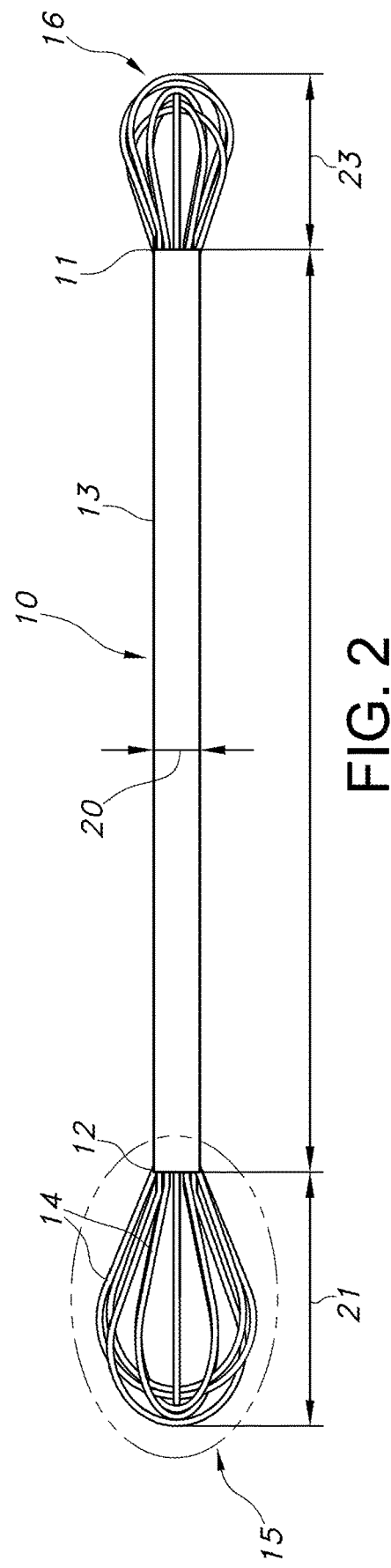

EAR CLEANING DEVICE WITH WHISK-LIKE BULBOUS ENDS

CROSS-REFERENCE TO RELATED APPLICATION(S)

This application is the U.S. National Phase of International Patent Application No. PCT/US2016/058099 filed on Oct. 21, 2016, which claims priority to U.S. Provisional Patent Application No. 62/257,012, filed on Nov. 18, 2015, the specifications of which are each incorporated herein by reference in their entirety for all purposes.

FIELD OF THE DISCLOSURE

The present disclosure is related to a flexible, disposable, ear cleaning device which is used to effectively remove debris and/or wax from the ears of a user, and in particular used in cleaning the ears of a human.

BACKGROUND

The most commonly used ear canal hygiene method known in the art today is a cotton swab such as Q-tips® cotton swabs. The swabs typically aid in the removal of water and some particulates from the ear, but are generally limited in effectively removing ear wax and excess ear debris that may accumulate in a human. Ear wax and any other ear debris can be shifted or lodged further towards the inner ear canal rather than removed. In addition, it may become even more difficult to clean the ear as the buildup may shift towards the inner ear and in effect, may result in inner ear infections and/or irritation that could lead to ear infections. Such shifts in wax buildup may also contribute to vertigo conditions.

There is also the problem with known ear cleaning tools such as Q-tips® or other cleaning tools, in that the application to the ear of such cleaning tools is known to strip the ear of wax. The ear canal in most individuals generally produces wax in order to water proof the ear canal, and prevent water from entering further into the inner portions of the ear. Otherwise, the removal of wax in such manner would allow the water to remain in the ear, which is known to contribute to problems such as temporary hearing loss, discomfort, vertigo conditions, and/or infections of the ear.

In addition, the wax in a person's ear is also known to act as a natural antibiotic and/or have anti-fungal properties being naturally acidic and in effect, the wax naturally prevents infections. Another known problem is that at the end of the ear canal lies the ear drum. The ear drum is near enough to the outside portion of the ear that inserting known ear cleaning tools may potentially reach or inadvertently push wax and/or debris in the inner canal and/or closer to the ear drum which is considered a very delicate part of the ear. Pressing on the little bones underlying, such as the hammer, anvil and the stirrup, located underneath the ear drum, sends shock waves into the inner ear which is responsible for hearing and balance. Therefore, merely tapping on the eardrum may cause problems that could affect both a user's hearing and balance among other possible complications.

A small amount of trauma to one's ear by use of, for example, a Q-tip® or other cleaning tool can cause, for example, benign paroxysmal positional vertigo. In addition, an acutely blocked ear may not clear so easily and may even be considered an untreatable emergency since there is a short time window within which one can treat the ear and/or determine whether an underlying serious condition that could impact hearing exists. Even sudden deafness can occur and may not be distinguishable from a temporary blocked ear, for example, an ear canal that is temporarily blocked by shifting the wax built up into the ear canal, which is known to diminish one's hearing temporarily.

Certain known stopper type ear cleaning devices including a loop curette wax extractor and a safety stopper is disclosed in U.S. Pat. Nos. 5,509,921, 5,888,199, 5,334,212 and 5,715,850. The problem with such a device is that it is non-disposable and more costly at the outset. In addition, such an ear cleaning device is required to be cleaned. As a result, there remains the danger of ineffective cleaning and/or subsequent scratching or scrapes to the skin with such use of devices, which can lead to infection. Additionally, the consumers are accustomed to having inexpensive, disposable instruments for which they pay a small price, rather than an expensive implement for cleaning their ears, which, in turn, has to be cleaned and maintained for proper and safe use.

Another known device is disclosed in U.S. Pat. No. 5,374,276. The use of a cotton swab for cleaning the auditory canal is disclosed. The cotton swab is removed and then discarded from the ear cleaning device. The ear cleaning device is intended to be reused. The consumer is expected to wrap and secure a cotton swab around the spiral hatch pattern on the one end of the handle portion of the ear wax remover. An extraction head on this ear wax remover comprises three similarly shaped projections extending radially outward from a shank. Each projection has the shape of a frustum of a cone. That is, the extraction head comprises three frustum cone shaped portions on the tip of the device. Thus, the ear wax remover tool is to be used repeatedly with subsequent swab attachments after each usage.

Another known device is disclosed in U.S. Pat. No. 7,658,745. This particular device is an ear cleaning device with an integral bulbous end. It includes openings at one end for scraping wax and debris and a distal end with plastic or cotton. The device also may similarly contribute to injury and/or infection of the ear as described hereinabove for the Q-tip® as the ear drum is considered a very delicate part of the ear and the bulbous ends (whether spoon like or a bulbous end with ridges) may also be inserted improperly by the consumer during removal of ear wax and/or debris.

Thus, there is a need for a new and improved ear wax cleaning device, which is small, light-weight, readily disposable and has a safer and more effective ear wax cleaning head, which is not in the form of a curette, or an integral scraper end, but which is made with whisk-like delicate flexible material to gently whisk away ear wax and/or debris without stripping the ear of all the wax which could lead to the above-described problems.

In order to overcome some of the disadvantages of known tools or devices for cleaning ears, is a need for a new and improved ear cleaning device, which is small, light-weight, readily disposable and provides a safer and effective ear cleaning end, which is not in the form of a curette, a scraper or spoon-like shape, but which is instead made with light-weight, flexible, balloon-like whisk end(s) including a series of whisk-like extensions that are joined at one or both ends of the device handle. Each whisk-like end is used to gently whisk away a top layer portion of collected ear wax and/or debris from the ears of a human.

SUMMARY

Embodiments of the disclosure will become apparent from the following detailed description considered in conjunction with the accompanying drawings. It is to be understood, however, that the drawings are designed as an illustration only and not as a definition of the limits of this disclosure.

The present disclosure provides for an ear cleaning device comprising an integral body, a central handle portion of the body to be gripped by the user, and a first whisk-like bulbous end integral with the central handle portion. The first whisk-like bulbous end is used for removing ear wax and/or debris by application of a whisk-like sweeping or whisk-like movement of the first whisk-like bulbous end to an outer ear.

In yet a further embodiment, the ear cleaning device further comprises a second whisk-like bulbous end integral with a second end of the central handle portion. In yet a further embodiment, disclosed is the ear cleaning device in which the first whisk-like bulbous end further includes multiple whisk-like loops that are integral with a first end of the central handle portion. In yet a further embodiment, the ear cleaning device further includes a second whisk-like bulbous end comprising multiple whisk-like loops that are integral with a second end of the central handle portion. In yet a further disclosed embodiment, is an ear cleaning device in which the whisk-like loops are spaced apart symmetrically prior to use.

In yet a further disclosed embodiment, the whisk-like loops are flexible and moldable thereby conforming to the shape and size of the outer ear of the user so as to be disposed of and retained within the outer portion of the ear thereby preventing insertion to an inner portion of the ear. In yet a further disclosed embodiment, the whisk-like loops are flexibly moldable thereby conforming to the shape and size of the outer ear of the user. In yet a further disclosed embodiment, at least the first whisk-like bulbous end is made of one or more of a low density polyethylene and a high density polyethylene.

In yet a further disclosed embodiment, the first whisk-like bulbous end is made of a soft flexible material comprising at least one of a polymer, polymeric material, silicon and plastic. In yet a further embodiment, the first whisk-like bulbous end of the ear cleaning device is made of a soft flexible material comprising at least one of a polymer, polymeric material, rubber, silicon polyethylene, and plastic. In yet a further embodiment, the first and second whisk-like bulbous ends are made of a soft flexible material comprising at least one of a polymer, polymeric material, rubber, silicon, polyethylene, and plastic. In yet a further embodiment, the first and second whisk-like bulbous ends are made of a soft flexible material that is hypoallergenic. In yet a further embodiment, the at least one whisk-like bulbous end is used for removal of other debris from the ear. It yet a further embodiment, at least one whisk-like bulbous end is flexible and moldable thereby gently conforming to the shape and size of the ear of the user when applied to the outer ear. In yet a further embodiment, at least one whisk-like bulbous end of the ear cleaning device is of a predetermined diameter. In yet a further embodiment, the at least one whisk-like bulbous end is of a predetermined size. In yet a further embodiment, the first whisk-like bulbous end is of a first predetermined size and the second whisk-like bulbous end is of a second predetermined size. In yet a further embodiment, the first and second whisk-like bulbous ends are both of a first predetermined size. In yet a further embodiment, the first whisk-like bulbous end includes multiple whisk-like loops that are expandable when applied to the outer portion of the ear thereby preventing the device from being disposed beyond the outer portion of the ear.

Further disclosed is an ear cleaning device wherein the first whisk-like bulbous end includes multiple whisk-like loops that include grooves extending along the periphery of one or more of the whisk-like loops, the grooves thereby collecting an outer layer of at least one of wax and debris during application of the whisk-like bulbous end to the outer ear. In yet a further embodiment, the ear cleaning device is disposable. In yet a further embodiment, the ear cleaning device is used for cleaning debris and/or ear wax from the outer ear of a human.

Other features of the present disclosure will become apparent from the following detailed description considered in conjunction with the accompanying drawings. It is to be understood, however, that the drawings are designed as an illustration only and not as a definition of the limits of the claims or the disclosure.

BRIEF DESCRIPTION OF THE DRAWINGS

FIG. 1 is a top perspective view of an ear cleaning device in accordance with an embodiment of the present disclosure;

FIG. 2 is a side view of an ear cleaning device in accordance with an embodiment of the present disclosure;

Figure 4:
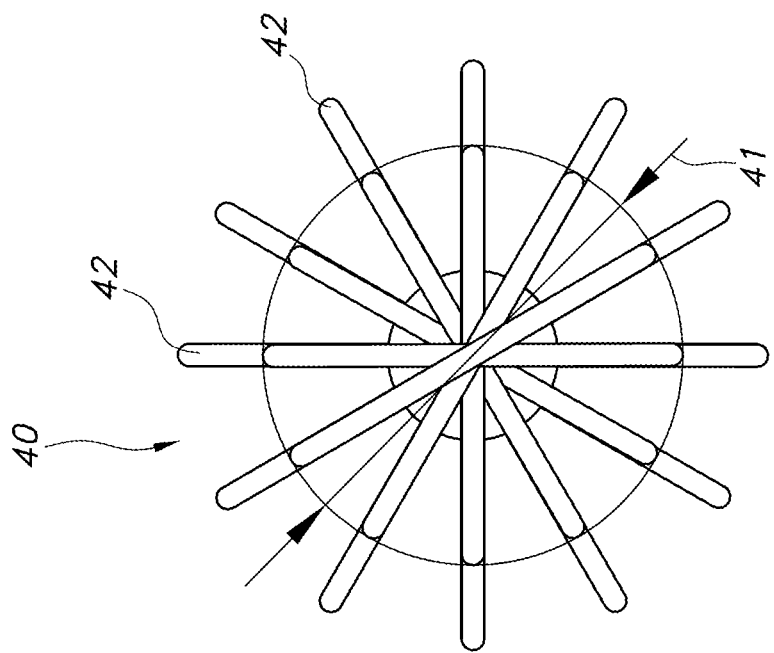
FIG. 4 is an additional cross-sectional view of the whisk-like bulbous end shown in FIG. 2 illustrating the radius thereof in accordance with the present disclosure.

It is to be appreciated that elements in the figures are illustrated for simplicity and clarity. Common but well-understood elements, which may be useful or necessary in a commercially feasible embodiment, are not necessarily shown in order to facilitate a less hindered view of the illustrated embodiments.

DETAILED DESCRIPTION

The following sections describe exemplary embodiments of the present disclosure. It should be apparent to those skilled in the art that the described embodiments of the present disclosure provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto.

Throughout the description, where items are described as having, including, or comprising one or more specific components, or where processes and methods are described as having, including, or comprising one or more specific steps, it is contemplated that, additionally, there are items of the present disclosure that consist essentially of, or consist of, the one or more recited components, and that there are processes and methods according to the present disclosure that consist essentially of, or consist of, the one or more recited processing steps.

As shown in the drawings for purposes of illustration, the ear cleaning device 10 comprises a main body portion 13 made of a lightweight, flexible material, for example, a flexible silicon or bendable plastic material, any one or more of a polymer, polymeric material, rubber, silicon and/or polyethylene, which is integral to and retains one or two whisk-like bulbous ends 15, 16. The whisk-like bulbous ends 15, 16 are integral with the body portion or handle 13. The whisk-like bulbous ends 15, 16 are lightweight, flexible or bendable and include multiple loop extensions 14 that are joined at a first distal end 12 and a second distal end 11 of the ear cleaning device 10. The whisk-like ends 15, 16 as shown in embodiment of FIG. 1 are disposed at the opposite ends of each of a handle portion 13. The handle portion 13 extends between the first bulbous end 15 and the second bulbous end 16 and in certain embodiments the ends 15, 16 are moldable to the shape and size of the user's ear canal at the time of use so as to prevent insertion into the inner ear canal and/or cause any shifting of accumulated wax and/or debris into the inner ear canal which can impinge upon and cause damage to a user's ear drum 61, as shown in FIG. 5.

Figure 5:
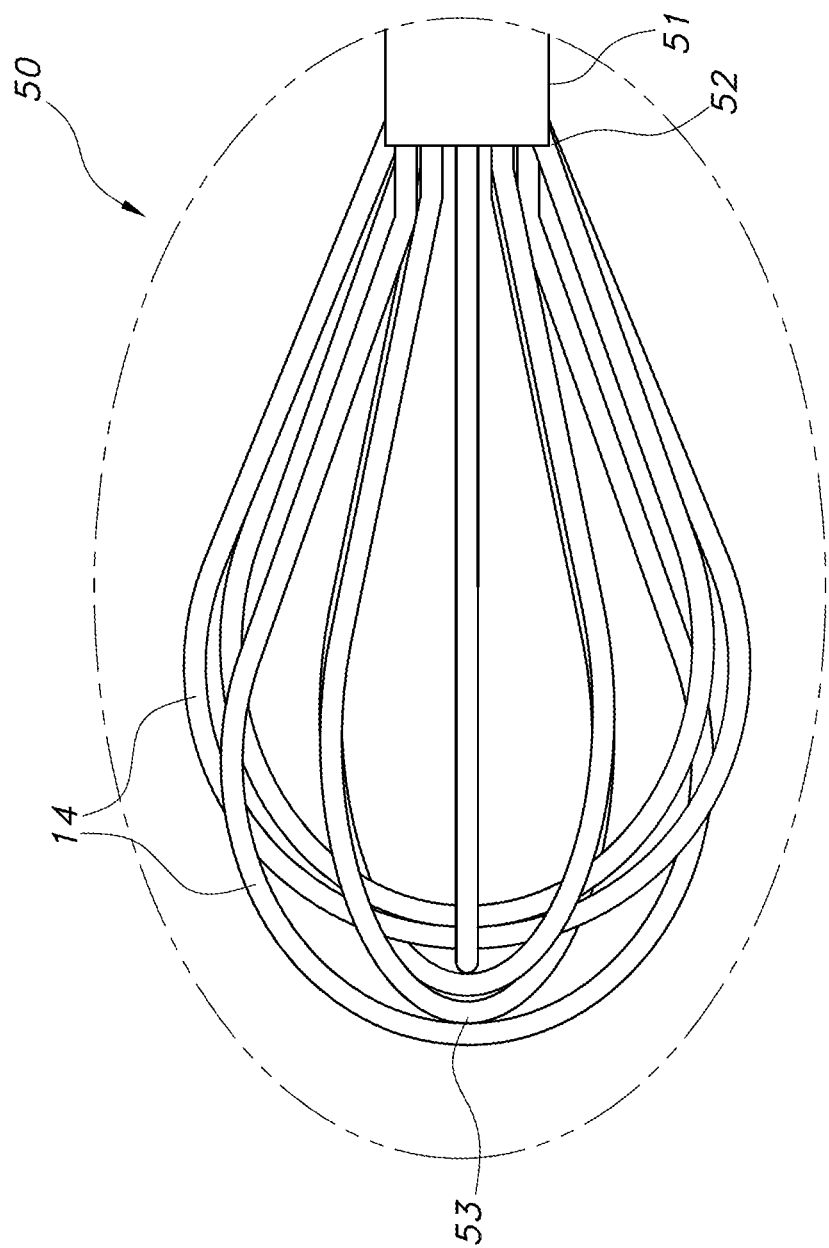
FIG. 5 is an enlarged plan view of one end of the ear cleaning device as shown in FIGS. 1 and 2.

As shown in FIG. 5, in accordance with a disclosed embodiment of the present disclosure, the bulbous ends 15, 16 can each be inserted into the outer ear 63 but, preventing any entrance into the ear canal 60. More particularly, the size of the bulbous ends 15, 16 are large enough to prevent any insertion into the ear canal 60 as the user gently whisks the outer ear portion 63 of accumulated wax and/or debris in a light, sweeping-like or whisk-like movement.

Figure 6:
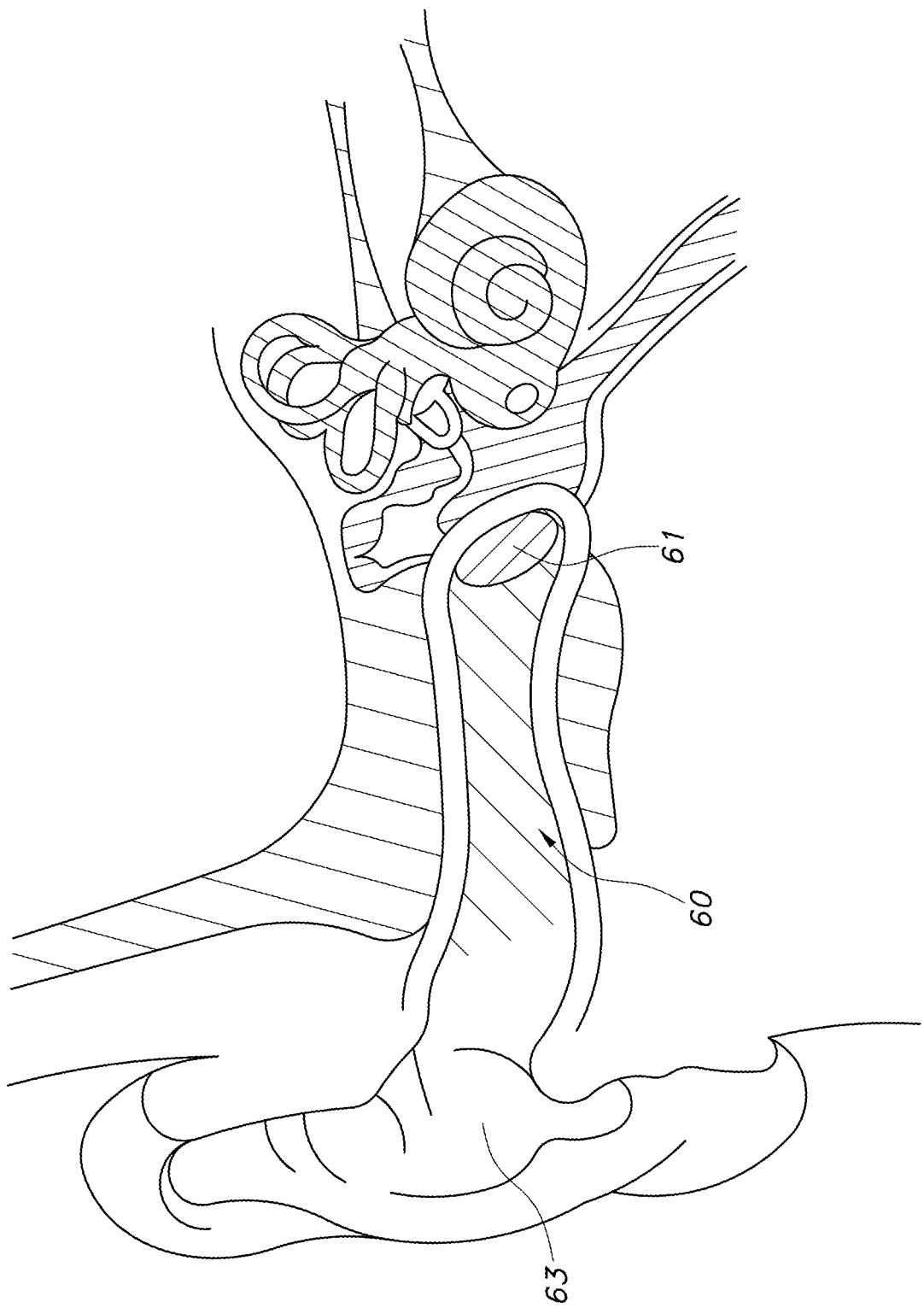
FIG. 6 is a view of an ear canal of a human to illustrate the areas of use of the ear cleaning device in accordance with the present disclosure.

In accordance with the illustrated embodiment as shown in FIG. 2, shown is the handle portion 13 which has a diameter 20 for example, of 0.2 cm which is similar or same as the diameter at distal ends 11, 12 of the handle portion 13 of the body portion 10. In addition, bulbous end 15 may be larger in length 21 than opposing bulbous end 16 to accommodate different sized outer ears 63 as shown in FIG. 6. The segment length 21 of bulbous end 15 may be for example 2.3 cm which is longer than the segment length 23 of 1.5 cm of end 16. It is noted that different sizes are used for the bulbous ends 15, 16 in order to prevent any unwanted entrance into the ear canal 60 of the user. The length of the segments 21, 23 may range generally between 0.5 cm to 2.5 cm in size. In addition, the bulbous ends 15, 16 in certain embodiments, are flexible and moldable to conform to the shape of the user's outer ear 63 so the cleaning device 10 can be inserted in a gentle whisk-like fashion, yet, large enough in diameter, for example, diameter 31 as shown in cross-section view FIG. 3, to prevent insertion into the inner ear 60.

In this regard, the bulbous ends 15, 16 of FIG. 1 or 2, are made in certain embodiments of various sizes that are suitable for the size of the user, and more notably, the size of the user's outer ear 63. The bulbous ends 15, 16 may be configured to have varying diameter sizes, to accommodate different sized ears such, as for example, that of children and adult-sized ears.

Figure 3:
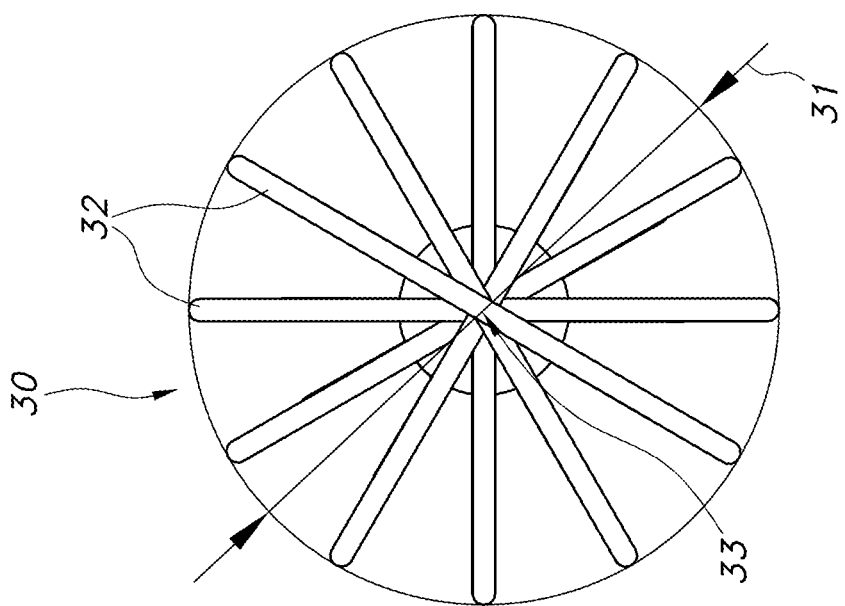
FIG. 3 is a cross-sectional view of the whisk-like bulbous end shown in FIG. 2 illustrating the diameter thereof in accordance with the present disclosure.

FIG. 3 is a cross-section view of bulbous ends 15, 16 as shown in FIG. 1 or 2. The whisk-like loops, wire-like loops or extensions 32 are joined at center point 33 in certain disclosed embodiments. The diameter 31 may range between, for example, smaller sizes such as 0.5 cm to larger widths such as 2 cm for larger, bulbous ends, 15, 16, having a wider girth or circumference.

FIG. 4 also shows a cross-sectional view with a diameter 41, which in certain embodiments varies in length depending on the size and diameter of the bulbous end(s) 15, 16 as configured for the particular size of the outer ear portion 63 of the user, thereby preventing any disposal of the device 10 past the outer ear 63 towards the inner ear portion 60 and further, eliminating any potential impact or trauma to the ear drum 61 of the user by preventing any shifting of wax and/or debris towards the ear drum 61. In FIG. 4, the diameter 41 is a smaller size than the diameter shown in FIG. 3, and is illustrated to show that the bulbous ends 15, 16 can vary in size to accommodate different sized ears.

It is noted that bulbous ends 15, 16 have smooth and rounded edges moldable to and thereby conforming to and defined by the overall shape of the outer ear 63 of the user as shown in FIG. 6.

Turning to FIG. 5, shown is an enlarged view of a whisk-like bulbous end 50 which includes an enlarged view of the whisk-like loops 14 that are intertwined and joined at end 52 at distal end 51 of the handle portion of the body 10 shown in FIGS. 1 and 2. In certain embodiments, the whisk-like loops may be permanently secured or fused together at distal end 53 so that a central point forms for guiding the application of the whisk-like bulbous tip 15 into the outer ear 63 as shown in FIG. 6 thereby, preventing disposal of the device past the outer ear portion. The central point forms at end 53, and in certain embodiments, also forms or is configured to include a circular stopper-like feature, that while guiding the application of the moldable and flexible whisk-like or wire-like flexible loops 14 into the outer ear 63, acts as a circular stopper portion to prevent the whisk-like bulbous end 50 from being inserted past the outer ear 63 into the inner ear canal 60. Such stopper-like feature also may include grooves throughout to allow for collection of wax and/or debris but, generally serves the purpose of prevention of trauma to the ear and/or displacement of the accumulated wax and/or debris in the outer ear towards the inner ear 60 and/or near or towards the ear drum 61.

FIG. 6 shows the outer ear area 63 which in a disclosed embodiment, the bulbous end 50 of the ear cleaning device is applied to gently scrape any debris or wax from the skin surface of the area 63. Area 60 shows the portion of the inner ear 60 for which the bulbous end 50 of the ear cleaning device 10 can not be inserted due to its bulbous shape which blocks access to the narrow pathway of the inner ear 60 and hence, preventing any inadvertent injury to the ear drum 61 and other portions of the inner ear.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate example embodiment.

Although preferred embodiments have been described herein with reference to the accompanying drawings, it is to be understood that the disclosure is not limited to those precise embodiments and that various other changes and modifications may be affected herein by one skilled in the art without departing from the scope or spirit of the embodiments, and that it is intended to claim all such changes and modifications that fall within the scope of this disclosure.

What is claimed is:

1. An ear cleaning device comprising:
    an integral body; and
    a central handle portion of the integral body that supports a first whisk-like bulbous end,
        the first whisk-like bulbous end being integral with the central handle portion, the first whisk-like bulbous end comprising flexible intertwined wire-like loops used in the removal of ear wax or debris, the first whisk-like bulbous end being of a size that averts insertion thereof to an ear canal.

2. The ear cleaning device in accordance with claim 1, wherein the device further comprises a second whisk-like bulbous end integral with a second end of the central handle portion.

3. The ear cleaning device in accordance with claim 2, wherein the first whisk-like bulbous end includes multiple whisk-like loops that are integral with a first end of the central handle portion.

4. The ear cleaning device in accordance with claim 3, wherein the whisk-like loops are spaced-apart symmetrically.

5. The ear cleaning device in accordance with claim 3, wherein the whisk-like loops are flexibly moldable.

6. The ear cleaning device in accordance with claim 4, wherein the whisk-like loops are flexibly moldable.

7. The ear cleaning device in accordance with claim 2, wherein the second whisk-like bulbous end includes multiple whisk-like loops that are integral with a second end of the central handle portion.

8. The ear cleaning device in accordance with claim 7, wherein the whisk-like loops are spaced-apart symmetrically.

9. The ear cleaning device in accordance with claim 7, wherein the whisk-like loops are flexibly moldable thereby conforming to the shape and size of an outer ear portion.

10. The ear cleaning device in accordance with claim 2, wherein the first and second whisk-like bulbous ends are made of a soft flexible material comprising at least one of a polymer, polymeric material, rubber, silicon and plastic.

11. The ear cleaning device in accordance with claim 2, wherein the first and second whisk-like bulbous ends are made of a soft flexible material that is hypoallergenic.

12. The ear cleaning device in accordance with claim 2, wherein the first whisk-like bulbous end is of a first predetermined size and the second whisk-like bulbous end is of a second predetermined size.

13. The ear cleaning device in accordance with claim 2, wherein the first and second whisk-like bulbous ends are both of a first predetermined size.

14. The ear cleaning device in accordance with claim 1, wherein at least the first whisk-like bulbous end is made of a mixture of a low density polyethylene and a high density polyethylene.

15. The ear cleaning device in accordance with claim 1, wherein at least the first whisk-like bulbous end is made of a flexible material.

16. The ear cleaning device in accordance with claim 1, wherein the first whisk-like bulbous end is made of a soft flexible material comprising at least one of a polymer, polymeric material rubber, silicon and plastic.

17. The ear cleaning device in accordance with claim 1, wherein at least one whisk-like bulbous end is used for removal of other debris from the ear.

18. The ear cleaning device in accordance with claim 2, wherein at least one whisk-like bulbous end is flexibly moldable thereby gently conforming to the shape and size of the ear of the user when applied.

19. The ear cleaning device in accordance with claim 2, wherein at least one whisk-like bulbous end is of a predetermined diameter.

20. The ear cleaning device in accordance with claim 2, wherein at least one whisk-like bulbous end is of a predetermined size.

21. The ear cleaning device in accordance with claim 1, wherein the first whisk-like bulbous end includes multiple whisk-like loops that are expandable when applied to the ear.

22. The ear cleaning device in accordance with claim 1, wherein the first whisk-like bulbous end includes multiple whisk-like loops that include grooves extending along the periphery of one or more of the whisk-like loops, the grooves thereby collecting an outer layer of at least one of wax and debris during application of the whisk-like bulbous end to the ear.

23. The ear cleaning device in accordance with claim 1, wherein the ear cleaning device is disposable.

24. The ear cleaning device in accordance with claim 1, wherein the ear cleaning device is used for removing debris and wax from an outer ear portion.

* * * * *